(12) United States Patent
Crea

(10) Patent No.: US 9,750,779 B2
(45) Date of Patent: Sep. 5, 2017

(54) JATROPHA CURCAS PROCESSING METHOD AND PRODUCTS

(75) Inventor: Roberto Crea, Hayward, CA (US)

(73) Assignee: AGROILS TECHNOLOGIES SRL, Florence (IT)

( * ) Notice: Subject to any disclaimer, the term of this patent is extended or adjusted under 35 U.S.C. 154(b) by 76 days.

(21) Appl. No.: 13/282,106

(22) Filed: Oct. 26, 2011

(65) Prior Publication Data

US 2013/0108716 A1    May 2, 2013

Related U.S. Application Data

(60) Provisional application No. 61/406,719, filed on Oct. 26, 2010.

(51) Int. Cl.

| | | |
|---|---|---|
| *A61K 36/47* | (2006.01) | |
| *C11B 1/04* | (2006.01) | |
| *C11B 1/06* | (2006.01) | |
| *C11B 1/10* | (2006.01) | |
| *A23K 10/37* | (2016.01) | |
| *A23K 50/10* | (2016.01) | |
| *A23K 50/75* | (2016.01) | |
| *A23K 50/30* | (2016.01) | |
| *A23K 50/80* | (2016.01) | |
| *A23L 11/30* | (2016.01) | |
| *A23L 25/00* | (2016.01) | |

(52) U.S. Cl.
CPC .............. *A61K 36/47* (2013.01); *A23K 10/37* (2016.05); *A23K 50/10* (2016.05); *A23K 50/30* (2016.05); *A23K 50/75* (2016.05); *A23K 50/80* (2016.05); *A23L 11/34* (2016.08); *A23L 25/00* (2016.08); *C11B 1/04* (2013.01); *C11B 1/06* (2013.01); *C11B 1/10* (2013.01); *A61K 2236/30* (2013.01); *Y02P 60/877* (2015.11)

(58) Field of Classification Search
None
See application file for complete search history.

(56) References Cited

U.S. PATENT DOCUMENTS 3,634,093 A * 1/1972 Huang .......................... 426/429
2013/0345456 A1  12/2013 Kirchner et al.

FOREIGN PATENT DOCUMENTS

| CN | 102090501 A * | 6/2011 |
|---|---|---|
| WO | WO 2010/092143 A1 | 8/2010 |
| WO | WO 2012/084730 A1 | 6/2012 |

OTHER PUBLICATIONS

Jemai et al. J. Agric. Food Chem. 2009, 57, 8798-8804.*
Shah et al. Industrial Crops and Products 20 (2004) 275-279.*
International Search Report for PCT/US2011/057896, dated Oct. 26, 2011, 4 pages.
Written Opinion of the International Search Authority for PCT/US2011/057896, dated May 31, 2012, 6 pages.
Ahmed et al. (2009) "Phorbol ester as toxic constituents of tropical Jatropha curcas seed oil," Eur. J. Sci. Res. 3:429-436.
Makkar et al. (2008) "Protein concentrate from Jatropha curcas screw-pressed seed cake and toxic and antinutritional factors in protein concentrate," J. Sci. Food. Agric. 88:1542-1548.
Saetae et al. (2011) "Functional properties of protein isolate obtained from physic nut (*Jatropha curcas* L.) seed cake," Food Sci. Biotechnol. 20(1):39-37.
Vernicia fordii. (Sep. 29, 2016). Retrieved from https://en.wikipedia.org/wiki/Vernicia_fordii.

* cited by examiner

*Primary Examiner* — Amy L Clark
(74) *Attorney, Agent, or Firm* — Lathrop Gage LLP; Giulio A. DeConti, Esq.

(57) ABSTRACT

A process for preparing a food or feed composition from *J. curcas* is disclosed. The method involves adding an acidified aqueous solution to *J. curcas* components, to a final pH of between 1 and 5, incubating the acidified mixture for a period for a period of at least 1 hour, and centrifuging the incubated mixture to separate the mixture into three physically distinct fractions: (i) a light, upper fraction containing oil, (ii) an aqueous fraction containing soluble acid-extracted components and breakdown products, and (iii) a substantially detoxified solid cake which forms or is used in forming the food or feed composition. The acidified aqueous solution added may be acidified olive vegetation water having a ratio of hydroxytyrosol to oleuropein of between 5:1 to 100:1. Also disclosed are a food or feed composition, and oil and aqueous fractions formed by the method.

7 Claims, No Drawings

JATROPHA CURCAS PROCESSING METHOD AND PRODUCTS

FIELD OF THE INVENTION

The present invention relates to a method for processing *Jatropha curcas* plants and products formed by the processing method.

BACKGROUND OF THE INVENTION

*Jatropha curcas* L. is a multipupose shrub of significant economic importance because of its several potential industrial and medicinal uses. *Jatropha curcas* L. or physic nut (or purging nut) is a drought resistant large shrub or small tree, belonging to the genus *Euphorbiaceae*, producing oil containing seeds. The species has its natural distribution area in the Northeastern part of South America. (Heller, 1996) and central Africa and several countries in Asia. The seeds of physic nut are a good source of oil, which can be used as a diesel substitute. They are used also in medicines, and soap and cosmetics manufacture in various tropical countries.

The fruit of *J. curcas* is green/yellow when fresh and contains seed. The seed and seed products of *J. curcas* are potentially a source of high nutritional value, e.g., as animal feed. The levels of essential amino acids, except lysine, in the seed cake are higher than that of the FAO/WHO reference protein for a five year old child in all the meal samples on a dry matter basis. The major fatty acids found in the oil samples were oleic (41.5-48.8%), linoleic (34.6-44.4%), palmitic (10.5-13.0%) and stearic (2.3-2.8%) acids. The residual protein-rich seed cake, remaining after extraction of the oil, could form a protein-rich ingredient in feeds for poultry, pigs, cattle and even fish if it could be detoxified.

Like the oil, the seed cake is toxic and therefore only suitable as animal feed after processing. The toxicity of *J. curcas* is based on several components (phorbol esters, curcains, trypsin inhibitors and others) which make complete detoxification a complicated process. Detoxification has been successful at laboratory scale (Gross et al., 1997; Martinez Herrera et al., 2006), but since the process is complicated, it is not suitable for small scale and local use. Large scale feed production, however, has to compete on a global market with high quality demands. Therefore, detoxification must be complete, constant and guaranteed, and is thus expected to be expensive. Hence, a successful penetration of *J. curcas* seed cake as feed to the market at a profitable price seems doubtful.

Toxic components. The main toxic components are phorbol esters, although in Mexico accessions without, or with low content of phorbol esters have been found (Rivera Lorca & Ku Vera, 1997; Martinez Herrera et al., 2006; Basha & Sujatha, 2007). The seed cake of this so called 'non' or 'low' toxic variety might be suitable for use as animal feed, but it still contains minor quantities of toxic components and resistance on the feed market towards this product is to be expected.

On the other hand, the seed cake is nutrient rich and therefore very suitable as fertilizer (Table 3). Together with the fruit coats, the major part of the nutrients can be recycled. When no fertilizers are used, which is assumed to be the case in the use of *J. curcas* as a low input crop, this recycling is necessary to maintain soil fertility, especially on non fertile marginal lands. Patolia (2007a) reported total above ground dry matter increase of 24% after 2 years.

Because of unavoidable inefficiencies, recycling nutrients will only be effective at a certain production level that allows a high dynamic nutrient cycle to take place. Initiating a plantation on low or non fertile soils therefore implies the need to use other fertilizers, at least at the start, to boost crop growth and seed production in the initial stages. The harvested part of *J. curcas* is the fruit, mostly containing three seeds. The seeds make up about 70% of the total weight of the fruit (30% fruit coat); the mature fruits have amoisture content of circa 15%, the seeds circa 7%. The oil is stored in the interior of the seed: the kernel, which makes up circa 65% of the total mass of the seed. The moisture contents are circa 10% for the hull and circa 5% for the kernel.

Oil fraction and quality. The seed of *J. curcas* contains a viscous oil, highly suitable for cooking and lighting by itself and for the production of biodiesel. The total fraction of oil, fats and carbohydrates is circa 30 to 35% for the seed and, since 99% of the oil is stored in the kernel, circa 50 to 55% for the kernel (Table 1).

The oil contains very little other components and has a very good quality for burning. Cetane number of *J. curcas* oil (23-41) is close to cottonseed (35-40) and better than rapeseed (30-36), groundnut (30-41) and sunflower (29-37) (Vaitilingom & Liennard, 1997). The toxicity of *J. curcas* is mainly based on phorbol esters and curcains, which give no pollution when burnt. The oil is also very suitable for transesterification into biodiesel (Mohibbe Azam et al., 2005).

The absence of sulphur dioxide ($SO_2$) in exhaust from diesel engines run on *J. curcas* oil shows that the oil may have a less adverse impact on the environment (Kandpal & Madan, 1995). As *J. curcas* oil has a higher viscosity than diesel oil (53 versus 8 cSt at 30 C), blending *J. curcas* oil up to 50% with diesel oil is advised for use in a Compression Ignition (C.I.) engine without major operational difficulties (Pramanik, 2003). Other publications mention much lower values for viscosity (17.1 cSt at 30 C), which would reduce the necessary blending fraction of diesel oil (Akintayo, 2004), however, conventional engines can be operated by blending biomethanol or bioethanol (with gasoline) or biodiesel (with diesel) from 3-20%. Some report that *J. curcas* oil should only be used as ignition accelerator (Forson et al., 2004).

Seed cake. Like the oil, the seed cake is toxic and therefore only suitable as animal feed after processing. The toxicity of *J. curcas* is based on several components (phorbol esters, curcains, trypsin inhibitors and others) which make complete detoxification complicated. Detoxification has been successful at laboratory scale (Gross et al., 16 1997; Martinez Herrera et al., 2006), but since the process is complicated, it is not suitable for small scale and local use. Large scale feed production, however, has to compete on a global market with high quality demands. Therefore, detoxification must be complete, constant and guaranteed, and is thus expected to be expensive. Hence, a successful penetration of *J. curcas* seed cake as feed to the market at a profitable price is challenging. The main toxic, but potentially medicinal, components are phorbol esters, although in Mexico accessions without, or with low content of phorbol esters have been found (Rivera Lorca & Ku Vera, 1997; Martinez Herrera et al., 2006; Basha & Sujatha, 2007). The seed cake of this so called 'non' or 'low' toxic variety might be suitable for use as animal feed, but it still contains minor quantities of toxic components and resistance on the feed market towards this product is to be expected.

On the other hand, the seed cake is nutrient rich and therefore very suitable as fertilizer. Together with the fruit coats, the major part of the nutrients can be recycled. When no fertilizers are used, which is assumed to be the casein the use of *J. curcas* as a low input crop, this recycling is necessary to maintain soil fertility, especially on non fertile marginal lands. Patolia (2007a) reported total aboveground dry matter increase. Because of unavoidable inefficiencies, recycling nutrients will only be effective at a certain production level that allows a high dynamic nutrient cycle to take place. Initiating a plantation on low or non fertile soils therefore implies the need to use other fertilizers, at least at the start, to boost crop growth and seed production in the initial stages.

The by-products of *J. curcas*, such as fruit coats, seed hulls and the remaining de-oiled seed cake after pressing, may be used for organic fertilization, or for the production of more energy. Seed hulls can be burnt and the seed cake and fruit pulp can be used for the production of biogas by anaerobic fermentation (Lopez et al., 1997; Staubmann et al., 1997; Vyas & Singh, 2007). By burning, most nutrients will be lost, but after fermentation, most nutrients will remain in the effluent that can still be used as a fertilizer to recycle nutrients. To maintain *J. curcas* production at a sustainable level, it is important to be aware that a huge amount of nutrients are removed if *J. curcas* byproducts are exploited for additional valorization. However, the range in the reported nutrient values only comes from a few sources (Table 3), with clear variation. This indicates that environmental and management conditions have a large effect on the eventual nutrient content of the various plant parts. Soil organic matter content decreases in a production system where nutrients are removed and not replenished by fertilization.

Oil extraction. For *J. curcas* oil extraction at small scale, various oil presses have been developed and modified from presses for other oil seed crops. They have in common that they vary in design and are non-standardized, as they were originally developed for other (edible) seeds and need to be optimized for *J. curcas* seeds. Bielenberg Ram (Hand) Presses handle 7-10 kg seed h-1 and spindle presses handle 15 kg seed h-1 (Mbeza et al., 2002). Commercially available pressing systems claim processing 500 kg seed h-1 (FIG. 15).

The recoverable oil fraction is clearly affected by pressing technology. For hand powered small scale pressing (such as the Bielenberg (Hand) Ram Press), an oil yield of only 19% of the seed dry weight or 30% of the kernel was reported (Foidl & Eder, 1997; Augustus et al., 2002; Akintayo, 2004; Henning, 2004; Francis et al., 2005), which is about 60% of the total extractable amount. With mechanized pressing equipment about 75% of the oil can be recovered. Commercially available pressing systems used for large-scale de-oiling of e.g. soybean and rapeseed reach up to 90%.

Modern extraction techniques can substantially raise the extractable oil fraction. Industrial extraction with organic solvents (mainly hexane) yield near 100% of the oil content, while extractions on water basis can yield from 65-97% of the oil, depending on, (a.o.) the composition of the extract solvent, the acidity (pH) and the temperature of the solvent (Shah et al., 2004; Shah et al., 2005).

Toxicity of the cake. A wide variation in toxic, but potentially medicinal, constituents, e.g. trypsin inhibitor in defatted kernels (18.4-27.5 mg g-1; Makkar et al., 1997) was observed, as well as a wide variation in saponins (1.8-3.4%; Makkar et al., 1997) and phytate (6.2-10.1%; Makkar et al., 1997). Phorbol esters are predominantly present, but are sometimes at low levels or not detected in provenances from Mexico. Phorbol ester content ranged from 0.87-3.32 mg g-1 of kernel weight in 17 provenances (Makkar et al., 1997; 3.85 mg g-1: Martinez Herrera et al., 2006).

Much attention to various aspects and tests of toxic components (phorbol esters and curcain) in *J. curcas* was reported at the '*Jatropha* 97' Symposium in Managua, Nicaragua (Chapter 4 in Gübitz et al., 1997), including experiences for using proteins from toxic and 'low toxic' *J. curcas* seeds for livestock feed (Makkar & Becker, 1997). Toxic constituents were found to be effective against a wide variety of pests (Solsoloy & Solsoloy, 1997; Rug & Ruppel, 2000). A 100% mortality rate was obtained against mosquito (Culex quinque fasciatus Say), when petroleum extracts of *J. curcas* leaves were used as a larvicide (Karmegam et al., 1997). The toxicity of *J. curcas* is based on several components (phorbol esters, curcains, trypsin inhibitors and others) that are present in considerable amounts in all plant components (including the oil), which make complete detoxification a complicated process.

Since the detoxification of *J. curcas* organic material is such a complicated process, it has—so far—only been successful at laboratory scale, and seems not to be suitable for small scale and local application. Like other *J. curcas* plant components, the seed cake is toxic and the prospect for successful penetration of the feed market with a detoxified product is challenging. The seed cake (either as remainder of the pressing process, or as a complete meal) is nutrient rich and therefore very suitable as fertilizer.

Phorbol esters of *J. curcas* decompose quickly as they are very sensitive to elevated temperatures, light and atmospheric oxygen (NIH, 2007); they decompose completely within 6 days (Rug & Ruppel, 2000).

To maintain *J. curcas* production at a sustainable level, it is important to take notion of the huge amount of nutrients that are removed from the soil if *J. curcas* by-products are exploited for additional uses, including the bio-refinery concept.

SUMMARY OF THE INVENTION

The invention includes, in one aspect, a process for preparing a food or feed composition from *J. curcas*. The method includes the steps of:

(a) forming a mixture containing *J. curcas* components, with addition of acid to a final pH of the mixture of between 1 and 5, (b) incubating the mixture for a period of at least 1 hour, and (c) centrifuging the incubated mixture to separate the slurry into three physically distinct fractions: (i) a light, upper fraction containing oil, (ii) an aqueous fraction containing soluble acid-extracted components and breakdown products, and (iii) a substantially detoxified solid cake which forms or is used in forming the food or feed composition.

In one embodiment, step (a) in the method includes crushing *J. curcas* to form a slurry, and acidifying the slurry to a pH of between 1-5. The slurry may be acidified by addition of acidified antioxidant solution. The acidified antioxidant solution may be added before, during, or after crushing the *J. curcas* components. The antioxidant solution may be olive vegetation water having ratio of hydroxytyrosol to oleuropein of between 5:1 to 100:1. In certain embodiments, the olive vegetation water comprises at least 0.1% (w/v) polyphenols. In other embodiments, the olive vegetation water comprises 5-10% (v/v) of an organic solvent. Preferred embodiments of organic solvents include methanol and ethanol.

In another embodiment, step (a) in the method includes crushing *J. curcas* to form a slurry, centrifuging the slurry to separate the slurry into three physically distinct fractions: (i)

a light, upper fraction containing oil, (ii) an aqueous fraction containing water-soluble components, and (iii) a first cake, and forming a cake slurry by addition of an acidified aqueous solution to the first cake, at a pH of between 1 and 5. The slurry may be formed by addition to the first cake of acidified antioxidant solution. The antioxidant solution may be olive vegetation water having ratio of hydroxytyrosol to oleuropein of between 5:1 to 100:1. In this embodiment, the light upper oil fraction from step (a) may be combined with the light upper oil fraction obtained in step (d), and the aqueous fraction from step (a) may be combined with the aqueous fraction obtained in step (d).

In still another embodiment, step (a) in the method includes adding an acidic aqueous solution to a first cake prepared from crushed *J. Curcas*, to form a cake slurry having a pH between 1-5. The cake slurry may be formed by addition to the first cake of acidified olive vegetation water having ratio of hydroxytyrosol to oleuropein of between 5:1 to 100:1. In certain embodiments, the olive vegetation water comprises at least 0.1% (w/v) polyphenols. In other embodiments, the olive vegetation water comprises 5-10% (v/v) of an organic solvent. Preferred embodiments of organic solvents include methanol and ethanol.

Acid or an acidic aqueous solution or acidified olive vegetation water may be added to the cake components in step (a) to a final pH of between 2-4, and an exemplary acidifying agent is a weak organic acid, such as citric acid.

The incubating step (c) may be carried out at room temperature for a period of at least one day, for a period of at least 10 days, or for a period of at least 30 days or longer.

The process may further include extracting soluble components from the aqueous fraction obtained in step (c), and/or concentrating the aqueous fraction by removal of water.

In the preceding embodiments, the *J. curcas* components are selected from the fruit, the seed, or an already formed cake of *J. curcas*. Also in the preceding embodiments, the olive vegetation water may comprise at least 0.1% (w/v) polyphenols. In other embodiments, the olive vegetation water comprises 5-10% (v/v) of an organic solvent. Preferred embodiments of organic solvents include methanol and ethanol.

In another aspect, the invention includes a food or feed comprising *J. curcas* from which have been removed, toxic components that are extracted and/or degraded by incubation of components in an acidified aqueous slurry at pH 1-5 for at least one day.

The composition may be prepared by the methods disclosed above.

Also disclosed is an oil fraction from *J. curcas* formed by the steps of:
(a) pressing *J. curcas* components to form a cake and oil and aqueous fractions,
(b) after removing the oil and aqueous fractions, adding an acidified aqueous solution to the cake to form a slurry having a final pH of between 1 and 5,
(c) incubating the slurry for a period for a period of at least 24 hours,
(d) centrifuging the incubated slurry to separate the slurry into three physically distinct fractions: (i) a light, upper fraction containing additional oil, (ii) an aqueous fraction containing soluble acid-extracted components and breakdown products, and (iii) a substantially detoxified solid cake which can be used as an animal feed, and
(e) isolating the light upper fraction obtained in step (d).

In one embodiment, step (a) includes adding the acidified antioxidant solution before, during, or after pressing the *J. curcas* components. In another embodiment, step (b) may be carried out by adding to the cake, in forming a slurry, acidified olive vegetation water having ratio of hydroxytyrosol to oleuropein of between 5:1 to 100:1. In certain embodiments, the olive vegetation water comprises at least 0.1% (w/v) polyphenols. In other embodiments, the olive vegetation water comprises 5-10% (v/v) of an organic solvent. Preferred embodiments of organic solvents include methanol and ethanol. The oil fraction may also includes the oil fraction obtained in step (a).

Further disclosed is an aqueous fraction from *J. curcas* formed by the steps of:
(a) pressing *J. curcas* components to form a cake and oil and aqueous fractions,
(b) after removing the oil and aqueous fractions, adding an acidified aqueous solution to the cake to form a slurry having a final pH of between 1 and 5,
(c) incubating the slurry for a period for a period of at least 24 hours,
(d) centrifuging the incubated slurry to separate the slurry into three physically distinct fractions: (i) a light, upper fraction containing additional oil, (ii) an aqueous fraction containing soluble acid-extracted components and breakdown products, and (iii) a substantially detoxified solid cake which can be used as an animal feed, and
(e) isolating the aqueous fraction obtained in step (d).

The aqueous fraction may also include the aqueous fraction of step (a). The aqueous fraction may be further treated to extract medicinal components therefrom. In one embodiment, step (a) includes adding the acidified antioxidant solution before, during, or after pressing the *J. curcas* components.

These and other objects and features of the invention will become more fully apparent when the following detailed description is read below.

In another aspect, provided herein is a method of extracting medicinal compounds from *J. curcas*, comprising the steps of:
(a) pressing *J. curcas* components to form a cake and oil and aqueous fractions,
(b) removing the oil and aqueous fractions and then adding an aqueous acid solution to the cake to form a slurry having a final pH of between 1 and 5,
(c) incubating the slurry for a period of at least 24 hours, and
(d) centrifuging the incubated slurry to separate the slurry into three physically distinct fractions: (i) a light, upper fraction containing additional oil, (ii) an aqueous fraction containing medicinal compounds and breakdown products, and (iii) a substantially detoxified solid cake.

In one embodiment, step (a) additionally comprises pressing the *J. curcas* components in the presence of an aqueous acid solution. In another embodiment, the aqueous acid solution is an antioxidant solution. In yet another embodiment, step (a) includes adding an acidified antioxidant solution before, during, or after the pressing of the *J. curcas* components. In certain embodiments, the antioxidant solution is olive vegetation water. The olive vegetation water may comprise at least 0.1% (w/v) polyphenols. The olive vegetation water may have a ratio of hydroxytyrosol to oleuropein of between 5:1 to 100:1. The olive vegetation water may comprise 5-10% (v/v) of an organic solvent. In a preferred embodiment, the organic solvent is selected from methanol and ethanol.

In another embodiment, the *J. curcas* components are selected from the fruit, the seed, or an already formed cake of *J. curcas*. In certain embodiments, the medicinal compounds are selected from curcin and phorbol esters.

DESCRIPTION OF THE INVENTION

In the present invention, acidulated water, also referred to as an acidic aqueous solution (e.g., citric acid 1%, chloridic acid 0.2 N or $H_2SO_4$ 0.2 N) may be used as a medium for extraction of hydrophobic compounds present in the cake. Among these hydrophobic compounds are most of the toxic compounds which make the cake poisonous. The aqueous extraction is carried at room temperature for few hours to several days. The suspension or slurry is then separated by a three phase centrifuge similar to than commonly used by the olive oil industry.

Three phase centrifugation will produce a "light" phase represented by the vegetable oil still trapped in the cake and thus recoverable by this process, the "heavy" phase, represented by the aqueous fraction containing the majority of the hydrophilic compounds, which includes Trypsin inhibitors, sorbol esters and lecitins (saponins), and the solid fraction (cake).

There are three different embodiments contemplated. In the first, *J. curcas* components are crushed in the presence of an acidified aqueous solution, to form a slurry, which is then incubated, e.g., 1 hour to 30 days, to extract and/or detoxify soluble compounds from the *J. curcas* cake components. After incubation, the slurry is centrifuged to form the three fractions, all of which form various aspects of the invention: an upper oil phase, an intermediate aqueous fraction containing extractable products, e.g., medicinal products, and a lower, detoxified cake, which may be further processed into a food or feed composition. In certain exemplary methods, the acidified aqueous solution that is added to the crushed *J. curcas* is an acidified olive vegetation water, that may be hydroxytyrosol-rich, having a pH preferably between 1-5 and containing a ratio of hydroxytyrosol to oleuropein of between 5:1 to 100:1. A suitable hydroxytyrosol-rich composition is disclosed in co-owned U.S. Pat. No. 6,416,808, which is incorporated herein in its entirety. Exemplary methods of obtaining olive vegetation water are described in co-owned U.S. Pat. Nos. 6,165,475 and 6,197,308, each of which are expressly incorporated herein by reference in their entirety. In certain embodiments and examples disclosed herein, the olive vegetation water is HIDROX® solution, an antioxidant solution prepared from olives.

In a second general embodiment, a *J. curcas* component slurry is first centrifuged to produce an upper oil fraction, an intermediate aqueous fraction and a lower cake. This initial step is preferably conducted under relatively neutral-pH conditions, e.g., pH 5-8. The initial cake is then further treated by addition of an acidified aqueous solution, e.g., the above acidified hydroxytyrosol-rich olive vegetation water, to form an acidified slurry, which is incubated as above, then centrifuged to form an upper oil fraction, an intermediate aqueous fraction, and lower, detoxified cake. The upper oil fraction may be combined with the initial oil fraction, and the aqueous fraction may be combined with the initial aqueous fraction. The aqueous fraction may be further concentrated and/or used as a source of extractable medical or other chemical components.

In a third general embodiment, an already formed *J. curcas* cake is used as the starting material, and to this cake is added an acidified aqueous solution, e.g., the above acidified hydroxytyrosol-rich olive vegetation water, to form a cake slurry which is incubated as above, then centrifuged to form an upper oil fraction, an intermediate aqueous fraction, and a lower, detoxified cake. In all of the preceding embodiments, the *J. curcas* components may be the fruit, the seed, or an already formed cake of *J. curcas*.

The presence of toxic/medicinal compounds in the aqueous fraction has been confirmed by HPLC analysis. The toxicity of the residual cake has been tested by animal toxicity studies conducted by BioQuant, Inc. San Diego.

The aqueous extraction method has the advantage to:
(a) recover the residual oil trapped in the pressed cake.
(b) extract and separate the toxic components present in the cake which are either hydrolyzed and/or are highly hydrophilic, and thus end up in the water fraction, and
c) render the solid fraction less or totally non-toxic as confirmed by animal studies.

Thus, the cake become a very valuable food and feed component which can be formulated in a variety of foods for human and animals.

The aqueous fraction becomes a very valuable raw material for further extraction and isolation of compounds of chemical and pharmaceutical use, and can be further concentrated to reduce the content in water. This can be easily accomplished by common steam or vacuum evaporators generally used in the juice industry (orange juice) as an example and then the water recycled for field irrigation or other uses in water deficient areas of the world. By performing the extraction of *J. curcas* with an acidified antioxidant solution, the chemical compounds thereby extracted are protected from decomposition during the extraction, storage and concentration.

The concentrated juice can finally be sold as raw material for the extraction and separation of valuable compounds for medical, industrial and other uses based upon the active molecules present in or isolated from the juice.

In one aspect, provided herein is a process for treating *J. curcas* comprising:
(a) forming a mixture containing *J. curcas* components, with addition of acid to a final pH of the mixture of between 1 and 5,
(b) incubating the mixture for a period of at least 1 hour, and
(c) centrifuging the incubated mixture to separate the mixture into three physically distinct fractions: (i) a light, upper fraction containing oil, (ii) an aqueous fraction containing soluble acid-extracted components and breakdown products, and (iii) a substantially detoxified solid cake which forms or is used in forming the food or feed composition.

In one embodiment, the process comprises the additional step: repeating steps (a)-(c).

In another embodiment, the process comprises the additional step: using the cake formed in step (c) as a food or feed composition.

In another embodiment of the process, step (a) includes crushing *J. curcas* components to form a slurry, and acidifying the slurry to a pH of 1-5.

In another embodiment of the process, step (a) includes acidifying the slurry by adding an acidified antioxidant solution. In yet another embodiment, step (a) comprises adding an acidified antioxidant solution before, during, or after crushing the *J. curcas* components. In still another embodiment, the antioxidant solution is olive vegetation water. In one embodiment, the olive vegetation water comprises at least 0.1% (w/v) polyphenols. In another embodiment, the olive vegetation water comprises 5-10% (v/v) of an organic solvent.

In another embodiment of the process, step (a) includes crushing *J. curcas* components to form a slurry, centrifuging the slurry to separate the slurry into three physically distinct fractions: (i) a light, upper fraction containing oil, (ii) an aqueous fraction containing water-soluble components, and (iii) a first cake, and forming a cake slurry by addition of an aqueous acid solution to the first cake, to a pH of between 1 and 5. In some embodiments of the process, the aqueous acid solution is an antioxidant solution. In some embodiments, the antioxidant solution is olive vegetation water.

In another embodiment of the process, the light upper oil fraction from step (a) is combined with the light upper oil fraction obtained in step (c).

In another embodiment of the process, the aqueous fraction from step (a) is combined with the aqueous fraction obtained in step (c).

In another embodiment of the process, the mixture formed in step (a) has a final pH of 2-4.

In another embodiment of the process, the mixture formed in step (a) is acidified by addition of a weak organic acid that imparts a final pH of 2-4 to the slurry. In some embodiments, the weak organic acid is citric acid.

In another embodiment of the process, the incubating step (b) is carried out at room temperature for a period of at least one day.

In another embodiment, the process further comprises extracting soluble components from the aqueous fraction obtained in step (c). In yet another embodiment, the process further comprises concentrating the aqueous fraction by removal of water.

In another embodiment of the process, the olive vegetation water comprises at least 0.1% (w/v) polyphenols. In yet another embodiment, the olive vegetation water has a ratio of hydroxytyrosol to oleuropein of between 5:1 to 100:1. In still another embodiment, the olive vegetation water comprises 5-10% (v/v) of an organic solvent.

In another embodiment of the process, the *J. curcas* components are selected from the fruit, the seed, or an already formed cake of *J. curcas*.

In another aspect, provided herein is a food or feed composition prepared according to the preceding process, and embodiments thereof.

In still another aspect, provided herein is an oil fraction obtained according to the preceding process, and embodiments thereof. In one embodiment, provided herein is the combined oil fractions of steps (a) and (c).

In yet another aspect, provided herein is an aqueous fraction obtained according to the preceding process, and embodiments thereof. In one embodiment, provided herein is the combined aqueous fractions of steps (a) and (c).

In one embodiment of the process, step (a) comprises:
(i) pressing *J. curcas* components to form a cake and oil and aqueous fractions, and
(ii) removing the oil and aqueous fractions, and then adding an aqueous acid solution to the cake to form a slurry having a final pH of between 1 and 5, and further comprising the step of: isolating the aqueous fraction obtained in step (c). In another embodiment, provided herein is the aqueous fraction obtained according to the process. In one embodiment, provided herein is the combined aqueous fractions of steps (a) and (c). In another embodiment, the aqueous fraction or fractions are further treated to extract medicinal compounds therefrom.

In another embodiment of the process, step (a) comprises:
(i) pressing *J. curcas* components to form a cake and oil and aqueous fractions, and
(ii) removing the oil and aqueous fractions, and then adding an aqueous acid solution to the cake to form a slurry having a final pH of between 1 and 5, and further comprising the step of: isolating the light upper oil fraction obtained in step (c). In another embodiment, provided herein is the oil fraction obtained according to the process. In one embodiment, provided herein is the combined oil fractions of steps (a) and (c).

In another aspect, provided herein is a method of extracting compounds from *J. curcas*, comprising the preceding processes and embodiments thereof. In one embodiment, the compounds are selected from curcin and phorbol esters.

Experimental

I. *Jathropa Curcas* Processing From Seed

Procedure A: To 200 kg seeds, prior to crushing, add the following solution A, made of 100 liters of 1% Citric Acid. Mix thoroughly to have a loose slurry and pour the mix onto a grinding machine. Grind mix into a wet pulp and pump slurry into kneading tank. Stir for about 1 hour at 30° C. Pump slurry into a three phase decanter and separate the three components, Solid pulp, oil and aqueous extract. Examine three components accordingly and calculate yields in oil. Save the solid fraction in freezer, until toxicity test is performed. Analyze aqueous fraction by HPLC.

Procedure B: To 200 kg seeds, prior to crushing, add the following solution B, made of 100 liters of 0.5% polyphenols extracted from the pulp of the olives in 1% citric acid. Mix thouroghly to obtain a slurry and proceed as above.

Procedure C: 200 kg seeds are processed without any addition of liquid. The solution A is added after the seeds are crushed into a thick paste and pumped into a tank for 1 hr. kneading. Proceed then as above in 1 and 2.

Procedure D: 200 kg seeds are processed without addition of any liquid. The solution B is added after the seeds are crushed into a thick paste and pumped into a tank for 1 hr. kneading. Proceed then as above in 1 and 2.

Procedure E (Control experiment): One kilogram of seeds are processed in a blender with addition of 500 ml water. The slurry is left at room temperature for 1.5 hrs and then centrifuged to separate liquid fraction from solid residue. Liquid is collected separately and analyzed by HPLC. The samples are frozen until further analysis is performed.

II. Processing From Solid Seed Cake

Procedure A1: To 200 kg dry cake add the following solution A, made of 100 liters of 1% Citric Acid directly into kneading tank. Stir for about 1.5 hour at 30° C. Pump slurry into a three-phase decanter and separate the three components: solid pulp, crude oil and aqueous extract. Examine three components accordingly and calculate yields in crude oil. Save the solid fraction in freezer until toxicity test is performed. Analyze aqueous fraction by HPLC.

Procedure B1: To 200 kg dry cake add the following solution B. made of 100 liters of 0.5% polyphenols extracted from the pulp of the olives in 1% citric acid. Mix thoroughly to obtain a slurry in kneading tank for 1.5 hrs at 30° C. and proceed as above.

Procedure E2 (Control experiment): One kilogram of dry seed cake is processed in a blender with addition of 500 ml water. The slurry is left at room temperature for 1.5 hrs and then centrifuged to separate liquid fraction from solid residue. Liquid is collected separately and analyzed by HPLC. The samples are frozen until further analysis is performed.

III. HPLC *Jatropha Curca* Processing and Detoxification.

1. HIDROX® 0.5% Liquid as antioxidant solution containing olive polyphenols (e.g., hydroxytyrosol) was obtained from Creagri, Inc. (Hayward, Calif.). The HPLC profile of HIDROX® 0.5% liquid is characterized by the presence of a large peak (RT=5 m) corresponding to hydroxytyrosol (HT) with a percent area of approximately 40% of total UV absorbing materials (Total Polyphenols, TP). A second small peak (RT=9.3 min.) corresponds to tyrosol. The area is approximately 10% of the HT area, 4% of total polyphenols (TP). The HPLC profile is then characterized by the presence of late peaks (at least 4-5) that elute at high concentration of methanol in Buffer A (RT from 19.5 m to 20.8 m). These peaks correspond to oleuropein, verbascoside and their aglycon derivatives, which contribute all together to 46-47% of the TP. Total UV area=41.5 million units.

2. Sample #1: *Jatropha Curcas* seeds (from Ghana) processed in the presence of 1% citric acid solution: The peaks of these chromatograms correspond to 100% compounds derived from the *Jatropha Curcas* (JC) and soluble in water (hydrophilic fraction). The front part of the spectrum is characterized by the presence of a large peak (RT=2 m) representing ca. 16-17% of the total UV areas, in a possible concentration of ca. 0.25% in weight of the total compounds in the solution (as direct comparison with 0.5% HIDROX® liquid). In addition, there are three additional peaks of relevance: the first one elutes with RT=1.6 m (3.5%), the second one with RT=2.4 m (3.8%) and the third one with RT=3.0 m (8.2%). A second set of peaks (three detectable) elutes with RT between 19.2 m and 20.0 m with percent areas of 4.5%, 6.3% and 4.0% respectively. Finally a third set of peaks (with two predominant peaks at RT=21.5 m and 21.8 m) is visible with a total % area of 22% (11.5% and 11% respectively). Total UV area=15.5 million units.

3. Sample #2: *Jatropha Curcas* cake (from the same source in Ghana) processed with HIDROX® 0.5% instead of 1% citric acid: The spectrum should contain the total compounds of #1 and #2 in a first approximation. The list of fast peaks eluting between RT=0 and RT=3.1 m include the large peak for JC (RT=2.0 m) which represents 21.2% of the total UV absorbing material, the two peaks at 5 m and 9.4 m (HT and Tyrosol (Ty) from HIDROX® 0.5%, the first representing HT (15.6%) and the second at 9.5 m representing Ty (1.7%). Also visible are the several peaks with low RT and high RT. Total UV area=49 million units. Observations: The total concentration of JC cake material in to HIDROX® 0.5% is approximately 8 million units in a total of 49 million units, or approximately 20%, assuming that the compounds in HIDROX® 0.5% are neither consumed nor diluted. The increase percentage of the JC peak at 2 m, (21.2%) vs. the HT peak area (15.6%), however seems to indicate that more than 60-65% of the JC cake compounds contribute to the total peak area of the extract. (Reduction of HT area from 37% to 15.6%, or 42% reduction). The Ty concentration is also reduced from 3.64% to 1.76%, or 48% reduction). The 3 peaks from JC cake are now present in 3.1%, 5.2% and 9.5%, which corresponds to an increase of 73% and 86%.

4. Sample #3: *Jatropha Curcas* seeds processed with HIDROX® 0.5%: The HPLC profile shows the presence of both peaks from HIDROX® 0.5% and JC. Specifically, from HIDROX® 0.5%, is well visible the HT peak RT=5.1 m (23.4%) and the Ty peak RT=9.4 m (2.1%). From the JC we clearly detect the peak at RT=2.0 m (7%) and the 3 additional peaks at RT=1.7 m (2.3%), RT=2.4 m (3%) and RT=3 m (9.7%). Total area: 31.5 million units.

5. Conclusions: Extraction with an acidified aqueous solution or an aqueous EtOH (ethanol) solution (5%) seem to provide similar results. The extraction with the above solutions may results in detoxification of both the oil and the biomass in that:
(a) some of the compounds detected by HPLC analysis correspond to phorbol esters (commercially available).
(b) the curcin (toxic protein) solubilizes in aqueous solutions.

In order to avoid oxidation of the above molecules in aqueous solution, it is necessary to introduce an antioxidant component, like hydroxytyrosol or other commercially available antioxidants. The antioxidants will perform better if the aqueous solution is acidified (citric acid or other organic and non-organic acids). The pH we have used is ranging between 3.0 and 5.0. The detoxifying solution (water/ antioxidant/acid and possibly some percentage of EtOH (5%) can be added to the *Jatropha Curcas* seeds prior to the milling and separation of the oil from the biomass (cake), or can be used on the dry cake to extract hydrophilic molecules and detoxify the biomass. Citric acid alone does not seem to protect from oxidation as the aqueous extract develops a strong odor after two-three months of storage. Experiments conducted at laboratory scale and pilot plant (200 kg seeds/cake) confirm the above. HPLC analysis of samples of the resulting aqueous fraction indicate that ca. 70-80% of the compounds in the solution derive from the extraction process. Subsequent use of the dry biomass as feed for fish has confirmed the lack of toxicity of it.

IV. Quantization of HT (hydroxytyrosol) in Freeze Dried Olive Juice by HPLC-Gradient Equipment and Reagents: HPLC grade methanol, $ddH_2O$, acetic acid and HIDROX® were used.

Standard Preparation: Accurately dilute stock solution of standard (100 mg/2 ml HT; Cayman Chemical) 1:3 with mobile phase (Solvent A) into a 2 ml micro tube. Mix well. The working concentration of the standard is 1.67 mg/ml.

Sample Preparation: Accurately weigh 100 mg +/−0.5 mg of sample and transfer to a 15 ml conical centrifuge tube. Add 10 ml of mobile phase (Solvent A) to the sample and mix well. Sonicate for 5 minutes then transfer 1 ml of dissolved sample to a 2 ml micro tube. Centrifuge the 1 ml sample at 11,000×g for 10 minutes. Remove all but the small pellet on the bottom to a new 2 ml micro tube.

Instrument Conditions:
Mobile Phase: (Solvent A): HPLC Grade $ddH_2O$ with 5% HPLC Grade
Methanol and 3% HPLC Grade Acetic Acid (pH 2.7-2.8). (Solvent B): 100% HPLC Grade Methanol
Flow Rate: 1.0 ml/min
Gradient: Solvent A (95.5%)/Solvent B (0.5%) isocratic for 20 min, then Solvent B 0.5-100% in 15 min.
Wavelength: OD 280 mm
Injection Volume: 20 μl
Column: Beckman Coulter Ultrasphere RP-C18 [4.6×150 mm]
Temperature: Column 20° C.+/−2° C.
Approximate Retention Times:
HT—5.9 minutes
Tyrosol—11.5 minutes
Procedure: Mix 920 ml of HPLC Grade $ddH_2O$ with 50 ml HPLC Grade Methanol and 30 ml HPLC Grade Acetic Acid "Solvent A"). Filter Solvent A with vacuum using a 0.45 micron Nalgene Filter. Condition the analytical column for 30 minutes before beginning calibration.

System Suitability: Prepare a standard solution by thawing (from −20° C. freezer) a stock HIDROX® solution (1.67 mg/ml). Once thawed, the standard is discarded. Inject the standard solution to demonstrate presence of HT, retention time, peak area, peak height, and plate number. Inject the standard solution 4 times to calibrate and establish the precision of the chromatographic system. Compute the relative standard deviation (% rsd) of the peak areas for HT. The system is considered suitable for assay if the % rsd of the four standard injections is <2%. As a further guide in assessing column performance, the column should develop ~9000 theoretical plates and the tailing factor should be less than 1.5. At the completion of the analysis, inject the standard solution as a calibration check. The calibration check should be +/−2% of the expected concentration.

Calculation: The concentration of HT is calculated as follows:

Asp/As×S×p×V×Ws=mg/g, wherein:
  Asp=Area of sample peak
  As=Area of standard peak
  S=working standard concentration in mg/ml
  P=purity of standard
  V=Sample Volume
  Ws=Sample Weight It is claimed:

1. A process for preparing a food or feed composition from *Jatropha curcas* comprising:
   (a) crushing or grinding at least 200 kg of one or more *Jatropha curcas* components to form a slurry, wherein the one or more *Jatropha curcas* components is a *Jatropha curcas* plant part selected from the group consisting of leaves, hulls, fruit, or seeds or pre-formed cake thereof;
   (b) acidifying the slurry of step (a) to a pH of 1-5 by adding an acidified aqueous antioxidant solution to form an acidified slurry;
   (c) incubating the acidified slurry for a period of at least 1 hour;
   (d) separating the incubated acidified slurry by centrifuging or decanting into three distinct fractions: (i) a fraction containing oil, (ii) an aqueous fraction comprising unoxidized phorbol esters and curcin, and (iii) a detoxified solid cake; and
   (e) further processing the detoxified cake to provide the a food or feed composition.

2. The process of claim 1, wherein the acidified aqueous antioxidant solution is olive vegetation water.

3. The process of claim 2, wherein the olive vegetation water has a ratio of hydroxytyrosol to oleuropein of between 5:1 to 100:1.

4. The process of claim 2, wherein the olive vegetation water further comprises 5-10% (v/v) of an organic solvent.

5. The process of claim 1, wherein the fraction containing oil is removed from the detoxified solid cake and aqueous fraction, and the detoxified cake and aqueous fraction is further separated to provide three physically distinct fractions.

6. The process of claim 1, wherein the fraction containing oil, the detoxified solid cake and the aqueous fraction are simultaneously separated from each other.

7. The process of claim 1, wherein the acidified slurry is acidified to a pH of 2-4.

* * * * *